United States Patent
Soon-Shiong

(10) Patent No.: US 11,510,982 B2
(45) Date of Patent: *Nov. 29, 2022

(54) HANK CETUXIMAB COMBINATIONS AND METHODS

(71) Applicant: NANTCELL, INC., Culver City, CA (US)

(72) Inventor: Patrick Soon-Shiong, Culver City, CA (US)

(73) Assignee: NantCell, Inc., Culver City, CA (US)

( * ) Notice: Subject to any disclaimer, the term of this patent is extended or adjusted under 35 U.S.C. 154(b) by 42 days.

This patent is subject to a terminal disclaimer.

(21) Appl. No.: 16/639,526

(22) PCT Filed: Aug. 14, 2018

(86) PCT No.: PCT/US2018/046735
§ 371 (c)(1),
(2) Date: Feb. 14, 2020

(87) PCT Pub. No.: WO2019/036485
PCT Pub. Date: Feb. 21, 2019

(65) Prior Publication Data
US 2020/0237908 A1    Jul. 30, 2020

Related U.S. Application Data

(60) Provisional application No. 62/545,744, filed on Aug. 15, 2017.

(51) Int. Cl.
| | | |
|---|---|---|
| *A61K 35/17* | (2015.01) | |
| *A61K 39/00* | (2006.01) | |
| *A61K 38/20* | (2006.01) | |
| *A61K 39/395* | (2006.01) | |
| *C12N 15/861* | (2006.01) | |
| *A61P 31/00* | (2006.01) | |
| *A61P 35/00* | (2006.01) | |
| *A61K 31/704* | (2006.01) | |
| *C07K 16/28* | (2006.01) | |

(52) U.S. Cl.
CPC ...... *A61K 39/39558* (2013.01); *A61K 31/704* (2013.01); *A61K 39/00117* (2018.08); *A61K 39/001152* (2018.08); *A61K 39/001164* (2018.08); *A61K 39/001182* (2018.08); *A61P 31/00* (2018.01); *A61P 35/00* (2018.01); *C07K 16/2818* (2013.01); *C07K 16/2827* (2013.01); *C07K 16/2863* (2013.01); *A61K 2039/507* (2013.01); *A61K 2039/523* (2013.01); *A61K 2039/5256* (2013.01); *A61K 2039/545* (2013.01); *A61K 2039/852* (2018.08)

(58) Field of Classification Search
None
See application file for complete search history.

(56) References Cited

U.S. PATENT DOCUMENTS

| | | | |
|---|---|---|---|
| 7,387,771 B1 | 6/2008 | Kratz | |
| 7,902,144 B2 | 3/2011 | Kratz | |
| 8,153,581 B2 | 4/2012 | Kratz | |
| 8,846,602 B2 | 9/2014 | Kratz | |
| 9,623,097 B2 * | 4/2017 | Palena | A61P 43/00 |
| 2015/0342975 A1 | 12/2015 | Geyer et al. | |
| 2016/0089388 A1 | 3/2016 | Levitt | |
| 2018/0222982 A1 * | 8/2018 | Dranoff | C07K 16/2818 |
| 2019/0134174 A1 * | 5/2019 | Jones | A61K 39/001106 |

FOREIGN PATENT DOCUMENTS

| | | |
|---|---|---|
| CA | 3 073 045 A1 | 2/2019 |
| CN | 110996991 A | 4/2020 |
| JP | 2020-531437 A | 11/2020 |
| KR | 10-2020-0033351 A | 3/2020 |
| WO | 2016/172249 A1 | 10/2016 |
| WO | 2016/205738 A2 | 12/2016 |
| WO | 2017/100709 A1 | 6/2017 |
| WO | 2018/209208 A1 | 11/2018 |
| WO | 2019/036485 A1 | 2/2019 |
| WO | 2019/050926 A1 | 3/2019 |

OTHER PUBLICATIONS

Sharp et al (Biomedicines, 2016, 4:19, internet pp. 1-13).*
Foy et al (Cancer Immunology Immunotherapy, 2016, 65:537-549).*
Foy et al (PLoS ONE, 2016, 11 :e0150084, internet pp. 1-18).*
Eralp et al (Breast Cancer Research, 2004, 6:R275-283).*
Wenneberg et al (Int. J. Cancer, 2013, 1643-1653).*
Yu etal (Clinical Cancer Research, 2010, 16:6019-6028).*
Klingemann et al (Frontiers in Immunology, 2016, 7:91, internet pp. 1-7).*
Van Audenaerde et al (Oncotarget, 2017, 8:56968-56979, published online May 25, 2017).*
Jochems et al (Oncotarget, 2016, 7:86359-86373).*
Tonn et al (Cytotherapy, 2013, 15:1563-1570).*
Eureka Alert! Public Release (Jan. 14, 2016) (https://www.eurekalert.org/pub_releases/2016-01/muos-mlf011416.php).*
Biospace.com (Apr. 11, 2016) (https://www.biospace.com/article/releases/altor-bioscience-corporation-partners-with-the-nci-to-further-develop-b-altor-s-b-alt-803-and-alt-801-cancer-immunotherapeutics-/).*
Chawla et al (JAMA Oncology, 2015, 1:1272-1280).*
Eilber et al (Journal of Clinical Oncology, May 30, 2017, 35, No. 15_suppl,abstract 11051).*
Mita et al (Invest New Drugs, 2015, 33:341-348).*
Hui-Chuou et al (2102, Annals of Plastic Surgery, 68:215-221).*
NCT03387111 Quilt 3.090 Clinical trial.gov, first posted Dec. 2017.*
Office Action received for Canadian Patent Application Serial No. 3073045 dated Feb. 3, 2021, 7 pages.

(Continued)

*Primary Examiner* — Laura B Goddard
(74) *Attorney, Agent, or Firm* — Martin Fessenmaier; Umberg Zipser LLP

(57) ABSTRACT

Contemplated cancer therapies comprise co-administration of aldoxorubicin with an immune therapeutic composition that preferably comprises a vaccine component and a cytotoxic cell component.

12 Claims, 4 Drawing Sheets

(56) References Cited

OTHER PUBLICATIONS

Notice of Reasons for Refusal received for Japanese Patent Application Serial No. 2020508476 dated Apr. 27, 2021, 8 pages (Including English Translation).
Gabitzsch et al., "The generation and analyses of a novel combination of recombinant adenovirus vaccines targeting three tumor antigens as an immunotherapeutic", Oncotarget, 2015, vol. 6, No. 31, pp. 31344-31359.
Pinette et al., "An IL-15-based super agonist ALT-803 enhances the NK cell response to cetuximab-treated squamous cell carcinoma of the head and neck", Cancer Immunology and Immunotherapy, 2019, 11 pages.
Extended European Search Report received for European Patent Application Serial No. 18846765.8 dated May 19, 2021, 9 pages.
Seery et al., "NANT cancer vaccine an orchestration of immunogenic cell death by overcoming immune suppression and activating NK and T cell therapy in patients with third line or greater metastatic pancreatic cancer", Journal of Clinical Oncology, 2019, vol. 37, No. 4, pp. 3 pages.
Examination Report No. 1 received for Australian Patent Application Serial No. 2018318125 dated Mar. 4, 2021, 5 pages.
Examination Report No. 3 received for Australian Patent Application Serial No. 2018318125 dated Jul. 29, 2021, 4 pages.
Examination Report No. 2 received for Australian Patent Application Serial No. 2018318125 dated May 20, 2021, 7 pages.
Jochems et al., "An NK cell line (haNK) expressing high levels of granzyme and engineered to express the high affinity CD 16 allele", Oncotarget, 2016, vol. 7, No. 52, p. 86359-86373.
Hui-Chou et al., "Short-term application of doxorubicin chemotherapy immunosuppressive side effects for composite issue allotransplantation", Annals of Plastic Surgery, Feb. 2012, vol. 68, No. 2, pp. 215-221.
International Search Report and Written Opinion received in PCT application Serial No. PCT/US2018/046735 dated Dec. 3, 2018, 14 pages.
Cytrx Corporation, "CytRx Corporation Announces Global Strategic License With NantCell Inc. For Aldoxorubicin, An Albumin Mediated Chemotherapeutic", PRNewswire, URL: https://www.prnewswire.com/news-releases/cytrx-corporation-announces-global-strategic-license-with-nantcell-inc-for-aldoxorubicin-an-albumin-mediated-chemotherapeutic-300495897.html, Jul. 28, 2017, 5 pages.
Martins Ines et al., "First Trial Assessing Engineered Natural Killer Cells in Cancer Patients to Begin Soon", Immuno-oncolgynews, URL: https://immuno-oncologynews.com/2017/01/31/nantkwest-first-trial-assessing-engineered-natural-killer-cells-cancer-patients/, Jan. 31, 2017, 7 pages.
Jochems et al., "ADCC employing an NK cell line (haNK) expressing the high affinity CD16 allele with avelumab, an anti-PD-L1 antibody", International Journal of Cancer, Aug. 1, 2017, vol. 141, No. 3, 22 pages.
International Preliminary Report on Patentability received in PCT application Serial No. PCT/US2018/046735 dated Feb. 27, 2020, 9 pages.
Mizadeh et al., "Doxorubicin Eliminates Myeloid-Derived Suppressor Cells and Enhances the Efficacy of Adoptive T Cell Transfer in Breast Cancer", Cancer Research, Jan. 1, 2014, vol. 74, No. 1, 24 pages.
Machiels et al., "Cyclophosphamide, Doxorubicin, and Paclitaxel Enhance the Antitumor ImmuneResponse of Granulocyte/Macrophage-Colony Stimulating Factor-secreting Whole-Cell Vaccines in HER-2/neu Tolerized Mice1", Cancer Research, May 1, 2001, pp. 3689-3697.
Hannesdóttir et al., "Lapatinib and doxorubicin enhance the Stat1-dependent antitumor immune response", European Journal of Immunilogy, 2013, vol. 43, pp. 2718-2729.
Zhang et al., "Chimeric Antigen Receptor-Engineered NK-92 Cells: An Off-the-Shelf Cellular Therapeutic for Targeted Elimination of Cancer Cells and Induction of Protective Antitumor Immunity", Frontiers Immunology, May 18, 2017, vol. 3, No. 533, pp. 1-17.
Park et al., "Doxorubicin enhances CD4+ T-cell immune responses by inducing expression of CD40 ligand and 4-1 BB" International Immunopharmacology, 2009, vol. 9, pp. 1530-1539.
Genßler etal., "Dual targeting of glioblastoma with chimeric antigen receptor-engineered natural killer cells overcomes heterogeneity of target antigen expression and enhances antitumor activity and survival", Oncoimmunology, Dec. 21, 2015, vol. 5, No. 4, 12 pages.
Fujii et al., "A potential therapy for chordoma via antibody-dependent cell-mediated cytotoxicity (ADCC) employing NK or high affinity NK (haNK) cells in combination with cetuximab", Journal Neurosurg, Jul. 28, 2017, vol. 128, No. 5, pp. 1-9.
Notice of Acceptance received for Australian Patent Application Serial No. 2018318125 dated Aug. 31, 2021, 3 pages.
Notice of Reasons for Refusal received for Korean Patent Application Serial No. 1020207007502 dated Aug. 18, 2021, 14 pages. (Including English Translation).
Rapoport et al., "Restoration of immunity in lymphopenic individuals with cancer by vaccination and adoptive T-cell transfer", Nature Medicine, 2005, vol. 11, No. 11, pp. 1230-1237.
Rapoport et al., "Supplementary drawing of Restoration of immunity in lymphopenic individuals with cancer by vaccination and adoptive T-cell transfer". Nature Medicine, 2005, vol. 11, No. 11, 1 page.
Office Action received for Canadian Patent Application Serial No. 3,073,045 dated Feb. 22, 2022, 4 pages.
Notification of Final Rejection received for Korean Patent Application Serial No. 10-2020-7007502 dated Feb. 23, 2022, 6 pages. (Including English Translation).
Decision to Grant a Patent received for Japanese Patent Application Serial No. 2020-508476 dated Apr. 1, 2022, 6 pages. (Including English Translation).
Notification of Reason for Refusal received for Korean Patent Application Serial No. 10-2022-7016167 dated Jun. 14, 2022, 11 pages. (Including English Translation).
Szczepanski et al., "Interleukin-15 enhances natural killer cell cytotoxicity in patients with acute myeloid leukemia by upregulating the activating NK cell receptors", Cancer Immunol Immunother, Springer, vol. 59, No. 1, 2010, pp. 73-79.

* cited by examiner

HANK CETUXIMAB COMBINATIONS AND METHODS

This application claims priority to our U.S. provisional application having the Ser. No. 62/545,744, filed Aug. 15, 2017, which is incorporated in its entirety herein.

PARTIES TO A JOINT RESEARCH AGREEMENT

The presently claimed invention was made by or on behalf of the below listed parties to a joint research agreement. The joint research agreement was in effect on or before the date the claimed invention was made, and the claimed invention was part of the joint research agreement and made as a result of activities undertaken within the scope of the joint research agreement. The parties to the joint research agreement are ETUBICS CORP, and NANTCELL, INC.

FIELD OF THE INVENTION

The field of the invention is compositions and methods for cancer treatment, especially as it relates to immune therapeutic drugs in combination with targeted forms of doxorubicin.

BACKGROUND

The following description includes information that may be useful in understanding the present invention. It is not an admission that any of the information provided herein is prior art or relevant to the presently claimed invention, or that any publication specifically or implicitly referenced is prior art.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Cetuximab (ERBITUX™, monoclonal antibody against human epidermal growth factor receptor) is approved for the treatment of metastatic colorectal cancer, metastatic non-small cell lung cancer and head and neck cancer, and for use in combination with radiation therapy for treating squamous cell carcinoma of the head and neck (SCCHN) or as a single agent in patients who have had prior platinum-based therapy. In addition to the direct inhibition of EGFR signal transduction, antibody-dependent cellular cytotoxicity (ADCC) through the recruitment of cytotoxic effector cells via the Fc portion of antibodies is thought to be an important mode of action of cetuximab.

Making use of the apparent dual targeting of cetuximab, genetically modified NK92 cells having a chimeric antigen receptor based on cetuximab was reported for glioblastoma (see e.g., OncoImmunology 2016). Similarly, high affinity NK (haNK) cells with a V158 variant of CD16 have been reported as a potentially more effective treatment modality as these cells have high levels of granzyme and high level of lytic activity even after irradiation. These cells were used in conjunction with cetuximab against a variety of cancer cells showing significant antibody-dependent cell-mediated cytotoxicity (Oncotarget, 2016, Vol. 7, (No. 52), pp: 86359-86373). While at least conceptually promising, an immune response using such approaches is still limited to the targeted effects of the antibody used. In addition, where the tumor microenvironment is suppressive, even such targeted approaches may not be as effective as anticipated.

Aldoxorubicin (((6-maleimidocaproyl) hydrazone of doxorubicin) is a prodrug form of doxorubicin that can be conjugated to thiol groups in various proteins, and especially to the cysteine thiol C34 in albumin when injected into an individual. Due to the acid labile nature of the hydrazine group, doxorubicin is hydrolytically cleaved from albumin once the doxorubicin-albumin conjugate encounters an acidic milieu as is often found in the cancer microenvironment. Therefore, aldoxorubicin is expected to specifically release free doxorubicin into the tumor microenvironment. Advantageously, circulating albumin also tends to preferentially accumulate in tumors, most likely due to gp60-mediated transcytosis through the endothelium of tumor neovasculature. Consequently, it is thought that aldoxorubicin presents an attractive therapeutic modality to specifically target the tumor microenvironment.

To that end, various clinical trials have been undertaken, including second-line treatment for glioblastoma (clinical trial identifier NCT02014844), treatment for Kaposi's sarcoma (clinical trial identifier 2029430), advanced or metastatic pancreatic ductal adenocarcinoma (clinical trial identifier NCT01580397), and metastatic small cell lung cancer (clinical trial identifier NCT02200757). Aldoxorubicin has also been reported in a combination with ifosfamide for treatment of metastatic or locally advanced sarcoma (clinical trial identifier NCT02235701). Notably, aldoxorubicin has not been used in combination with immune therapeutic agents, presumably due to suspected adverse effects from DNA damage response, and epigenetic and transcriptomic deregulation in various cells exposed to doxorubicin.

Thus, even though limited combinations of aldoxorubicin in the treatment of cancer are known in the art, there is still a need to provide improved combination therapies, particularly in combination with immune therapeutic compositions.

SUMMARY OF THE INVENTION

The inventive subject matter is directed to various compositions, methods, and uses of combination of immune therapeutic compositions and chemotherapeutic compositions to treat a tumor, especially in metastatic tumors. Most notably, co-administration of a chemotherapeutic composition including aldoxorubicin enhanced immune response against a tumor where the immune therapeutic compositions include cancer vaccines against one or more tumor associated antigens and NK cell-based therapeutics. Advantageously, therapeutic benefits of both haNK cells as well as aldoxorubicin are not adversely impacted by a hypoxic tumor microenvironment. Indeed, myeloid-derived suppressor cells (MDSC) commonly found in a hypoxic tumor microenvironment can be reduced or even eliminated using doxorubicin (preferentially released from aldoxorubicin in the acidic tumor microenvironment).

In one aspect of the inventive subject matter, the inventors contemplate a method of treating a patient having a tumor. In this method, an immune therapeutic composition comprising a vaccine component and a cytotoxic cell component and a chemotherapeutic composition comprising aldoxorubicin are provided. Then, the immune therapeutic composition and the chemotherapeutic composition are administered to the patient in a dose and schedule sufficient to treat the tumor (e.g., a solid tumor, a metastatic tumor, etc.). Preferably, the patient treated with such method has a medical history of at least one of previous platinum-based chemotherapy and previous anti-PD-1/PD-L1 therapy.

In especially preferred aspects, the vaccine component comprises at least one or two of a modified bacterium, a modified yeast, and a modified virus. It is preferred that the vaccine component comprises a recombinant nucleic acid that encodes a tumor associated antigen (e.g., brachyury, MUC1, and CEA). It is still further preferred that the cytotoxic cell component is at least one of a haNK cell and a T cell, and the haNK cell or the T cell is genetically engineered to express at least one of a chimeric antigen receptor and a CD16 high-affinity variant.

Suitable methods may also include a step of administering an antibody or a protein that interferes with or down-regulates checkpoint inhibition, which may be coupled to the cytotoxic cell component, for example, via CD16 of a haNK cell. For example, suitable antibodies will selectively bind to a growth factor receptor, a blood vessel growth receptor, a tumor associated antigen, a tumor specific antigen, or a tumor- and patient-specific neoepitope. In addition, the protein that interferes with or down-regulates checkpoint inhibition may be an antibody or an antagonist of CTLA-4, PD-1, TIM1 receptor, 2B4, or CD160.

Where desired, contemplated methods may also include a step of administering an immune stimulatory cytokine (e.g., IL-2, IL-15, etc.) or immune stimulatory superkine (e.g., ALT803). Most typically, it is contemplated that the vaccine component and the cytotoxic cell component are separately administered by at least one day. However, it is contemplated that the vaccine component and the cytotoxic cell component are administered concurrently or at least on the same day. Optionally, a molecular profile of the patient, especially that includes HER2 expression level or a RAS mutation status can be determined before and after the treatment according to this method, which may provide guidance for determining a likelihood of success of the treatment, determining the types of antibodies in the treatment, and further treatment plans.

In another aspect of the inventive subject matter, the inventors contemplate a use of an immune therapeutic composition and a chemotherapeutic composition comprising aldoxorubicin in the treatment of a patient having a tumor. Preferably, the patient treated with such method has a medical history of at least one of previous platinum-based chemotherapy and previous anti-PD-1/PD-L1 therapy. The immune therapeutic composition comprises a vaccine component and a cytotoxic cell component, and further optionally, comprises an antibody that specifically binds to a growth factor receptor, a blood vessel growth receptor, a cancer associated antigen, a cancer specific antigen, or a cancer- and patient-specific neoepitope or a protein that interferes with or down-regulates checkpoint inhibition.

In especially preferred aspects, the vaccine component comprises at least one or two of a modified bacterium, a modified yeast, and a modified virus. It is preferred that the vaccine component comprises a recombinant nucleic acid that encodes a tumor associated antigen (e.g., brachyury, MUC1, and CEA). It is still further preferred that the cytotoxic cell component is at least one of a haNK cell and a T cell, and the haNK cell or the T cell is genetically engineered to express at least one of a chimeric antigen receptor and a CD16 high-affinity variant. In some embodiments, the cytotoxic cell component is coupled with an antibody or a protein that interferes with or down-regulates checkpoint inhibition. It is preferred that the antibody specifically binds to at least one of a growth factor receptor, a blood vessel growth receptor, an immune checkpoint inhibitor, a tumor associated antigen, a tumor specific antigen, or a tumor- and patient-specific neoepitope. It is also preferred that the protein that interferes with or down-regulates checkpoint inhibition is an antibody or an antagonist of CTLA-4, PD-1, TIM1 receptor, 2B4, or CD160.

In some embodiments, the vaccine component and the cytotoxic cell component are formulated to be co-administered to the patient. In other embodiments, the vaccine component and the cytotoxic cell component are formulated to be separately administered to the patient.

The use can further comprise a use of an immune stimulatory cytokine or immune stimulatory superkine in the treatment. Most preferably, the immune stimulatory cytokine or immune stimulatory superkine is selected from the group consisting of IL-2, IL-12, IL-15, IL-15 super agonist (ALT803), IL-21, IPS1, and LMP1.

Various objects, features, aspects and advantages of the inventive subject matter will become more apparent from the following detailed description of preferred embodiments along with the accompanying drawings.

DETAILED DESCRIPTION

Figure 1:
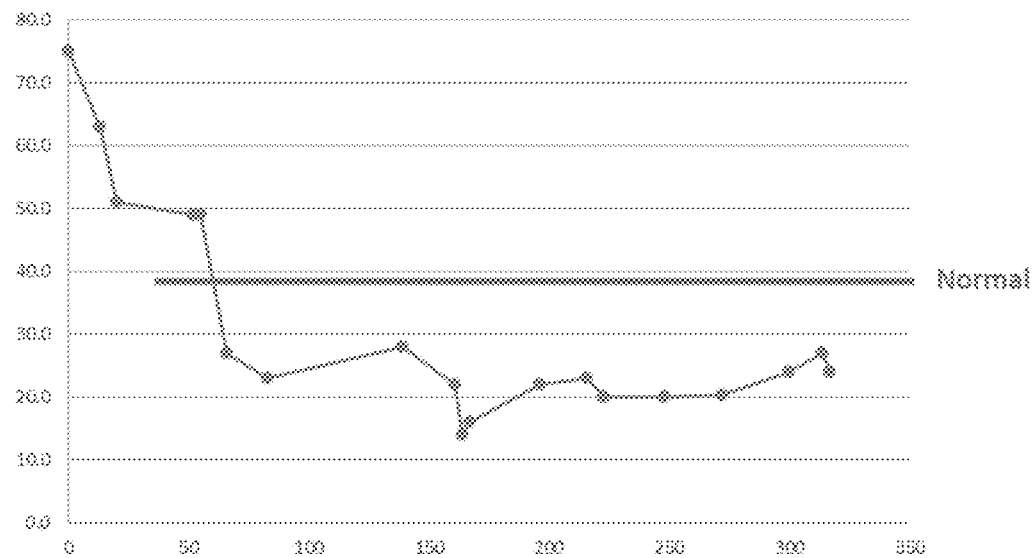
FIG. 1 shows a graph of normalized carbohydrate antigen (CA) 19-9 (CA19-9) level in patient's blood after cancer vaccine and cytotoxic cell treatment to patient #1 diagnosed with metastatic pancreatic cancer. The x-axis represents days (time) and y-axis represents quantity.

The inventors have now discovered that the effectiveness of immune therapeutic compositions and a chemotherapeutic agent including aldoxorubicin can be enhanced, in some cases even synergistically (i.e., to a more-than-additive extent), by co-administration of those two agents to a cancer patient. Viewed from a different perspective, the inventors further found that a tumor, especially a metastatic tumor, in a patient can be more effectively treated by providing a treatment regimen including immune therapeutic compositions and a chemotherapeutic agent including aldoxorubicin. Such finding is unexpected and even surprising as aldoxorubicin is a precursor of doxorubicin, and as doxorubicin has been reported as an immune suppressant (see e.g., Ann Plast Surg. 2012 February; 68(2):215-21). Therefore, in an especially preferred aspect, the inventors contemplate that a treatment regimen including an immune therapeutic composition comprising i) a vaccine component and a cytotoxic cell component, and ii) a chemotherapeutic composition comprising aldoxorubicin can be provided, and that such treatment regimen can be used to treat the tumor by administering the immune therapeutic composition and the chemotherapeutic composition in a dose and schedule sufficient to treat the tumor.

As used herein, the term "tumor" refers to, and is interchangeably used with one or more cancer cells, cancer tissues, malignant tumor cells, or malignant tumor tissue, that can be placed or found in one or more anatomical locations in a human body. As used herein, the term "bind" refers to, and can be interchangeably used with a term "recognize" and/or "detect", an interaction between two molecules with a high affinity with a KD of equal or less than 10−6M, or equal or less than 10−7M. As used herein, the term "provide" or "providing" refers to and includes any acts of manufacturing, generating, placing, enabling to use, or making ready to use.

As used herein, the term "co-administering" or "co-administration" refers to administering two or more agents to a patient in a single treatment regimen. Thus, co-administering agent A and agent B may refer concurrent administrating of agent A and agent B to a patient in a single formulation or in two separate formulations. Also, co-administering agent A and agent B may refer administering of agent A and agent B according to a single treatment regimen with a purpose of targeting a single tumor. For example, a treatment regimen for treating the tumor for patient A may comprise administering agent A in day 1 and administering agent B in day 2, and repeat such administrations for 2 weeks. In such example, agent A and agent B are considered to be co-administered to the patient A.

In most preferred aspect, the vaccine component is at least one of, or at least two of a modified bacterium, a modified yeast, or a modified virus that includes a recombinant nucleic acid encoding a tumor associated antigen. Any suitable tumor associated antigens that can elicit immune response by immune cells in the tumor microenvironment are contemplated. Thus, the tumor associated antigens may include, but not limited to, a tumor-associated antigen such as MUC1, CEA, brachyury, RAS (e.g., a mutated RAS (e.g., RAS with G12V, Q61R and/or Q61L mutations, etc.)), a tumor-specific antigen such as PSA, PSMA, HER2, or tumor- and patient-specific neoantigen or neoepitope, which can be identified from the patient's omics data. In some embodiments, each of the modified bacterium, a modified yeast, or a modified virus may include a recombinant nucleic acid encoding a single tumor-associated antigen. In other embodiments, at least one of the modified bacterium, a modified yeast, or a modified virus may include a recombinant nucleic acid encoding two or more tumor-associated antigens as a polytope.

As used herein, a polytope refers a tandem array of two or more antigens expressed as a single polypeptide. Preferably, two or more human disease-related antigens are separated by linker or spacer peptides. Any suitable length and order of peptide sequence for the linker or the spacer can be used. However, it is preferred that the length of the linker peptide is between 3-30 amino acids, preferably between 5-20 amino acids, more preferably between 5-15 amino acids. Also inventors contemplates that glycine-rich sequences (e.g., gly-gly-ser-gly-gly, etc.) are preferred to provide flexibility of the polytope between two antigens.

In some embodiments, the recombinant nucleic acid in the vaccine component may also include one or more nucleic acid sequences that encode one or more co-stimulatory molecules. The co-stimulatory molecules may include B7.1 (CD80), B7.2 (CD86), CD30L, CD40, CD40L, CD48, CD70, CD112, CD155, ICOS-L, 4-1BB, GITR-L, LIGHT, TIM3, TIM4, ICAM-1, LFA3 (CD58), and members of the SLAM family. Moreover, the nucleic acid may further include a sequence encoding a cytokine (e.g., IL-2, IL-7, IL-12, IL-15, an IL-15 superagonist (IL-15N72D), and/or an IL-15 superagonist/IL-15RαSushi-Fc fusion complex). Alternatively, or additionally, the nucleic acid further may also include a sequence encoding at least one component of a SMAC (e.g., CD2, CD4, CD8, CD28, Lck, Fyn, LFA-1, CD43, and/or CD45 or their respective binding counterparts). Where desired, the nucleic acid may additionally comprise a sequence encoding an activator of a STING pathway, such as a chimeric protein in which a transmembrane domain of LMP1 of EBV is fused to a signaling domain of IPS-1. Such modifications are thought to even further enhance development of an adaptive immune response by providing additional signals for activation of the adaptive immune response.

It is contemplated that the recombinant nucleic acids contemplated herein need not be limited to viral, yeast, or bacterial expression vectors. Alternatively, the recombinant nucleic acids may also include DNA vaccine vectors, linearized DNA, and mRNA, all of which can be transfected into suitable cells following protocols well known in the art.

Any suitable methods to generate a vaccine component are contemplated. Most typically, the nucleic acid sequence encoding a tumor associated antigen can be placed in an expression vector. The recombinant nucleic acid are inserted in the vector such that nucleic acid can be delivered to an antigen presenting cell (e.g., dendritic cells, etc.) of the patient, or to transcribe the nucleic acid sequence in bacteria or yeast so that the recombinant protein encoded by the nucleic acid sequence can be, as a whole, or as fragments, delivered to the antigen presenting cell. Any suitable expression vectors that can be used to express protein are contemplated. Especially preferred expression vectors may include those that can carry a cassette size of at least 1 k, preferably 2 k, more preferably 5 k base pairs.

Thus, in one embodiment, a preferred expression vector includes a viral vector (e.g., nonreplicating recombinant adenovirus genome, optionally with a deleted or non-functional E1 and/or E2b gene). Where the expression vector is viral vector (e.g., an adenovirus, and especially AdV with E1 and E2b deleted), it is contemplated that the recombinant viruses including the recombinant nucleic acid may then be individually or in combination used as a therapeutic vaccine in a pharmaceutical composition, typically formulated as a sterile injectable composition with a virus titer of between $10^6$-$10^{13}$ virus particles, and more typically between $10^9$-$10^{12}$ virus particles per dosage unit. Alternatively, virus may be employed to infect patient (or other HLA matched) cells ex vivo and the so infected cells are then transfused to the patient. In further examples, treatment of patients with the virus may be accompanied by allografted or autologous natural killer cells or T cells in a bare form or bearing chimeric antigen receptors expressing antibodies targeting neoepitope, neoepitopes, tumor associated antigens or the same payload as the virus. The natural killer cells, which include the patient-derived NK-92 cell line, may also express CD16 and can be coupled with an antibody.

In still further embodiments, the expression vector can be a bacterial vector that can be expressed in a genetically-engineered bacterium, which expresses endotoxins at a level low enough not to cause an endotoxic response in human cells and/or insufficient to induce a CD-14 mediated sepsis when introduced to the human body. One exemplary bacteria strain with modified lipopolysaccharides includes ClearColi® BL21(DE3) electrocompetent cells. This bacteria strain is BL21 with a genotype F– ompT hsdSB (rB–mB–) gal dcm lon λ(DE3 [lad lacUV5-T7 gene 1 ind1 sam7 nin5]) msbA148 ΔgutQΔkdsD ΔlpxLΔlpxMΔpagPΔlpxPΔeptA. In this context, it should be appreciated that several specific deletion mutations (ΔgutQ ΔkdsD ΔlpxL ΔlpxMΔpagPΔlpxPΔeptA) encode the modification of LPS to Lipid IVA, while one additional compensating mutation (msbA148) enables the cells to maintain viability in the presence of the LPS precursor lipid IVA. These mutations result in the deletion of the oligosaccharide chain from the LPS. More specifically, two of the six acyl chains are deleted. The six acyl chains of the LPS are the trigger which is recognized by the Toll-like receptor 4 (TLR4) in complex with myeloid differentiation factor 2 (MD-2), causing activation of NF-κB and production of proinflammatory cytokines. Lipid IVA, which contains only four acyl chains, is not recognized by TLR4 and thus does not trigger the endotoxic response. While electrocompetent BL21 bacteria is provided as an example, the inventors contemplates that the genetically modified bacteria can be also chemically competent bacteria. Alternatively, or additionally, the expression vector can also be a yeast vector that can be expressed in yeast, preferably, in *Saccharomyces cerevisiae* (e.g., GI-400 series recombinant immunotherapeutic yeast strains, etc.).

The inventors further contemplated that the recombinant virus, bacteria or yeast having recombinant nucleic acid as described above can be further formulated in any pharmaceutically acceptable carrier (e.g., preferably formulated as a sterile injectable composition) to form a pharmaceutical composition. Where the pharmaceutical composition includes the recombinant virus, it is preferred that a virus titer of the composition is between $10^4$-$10^{12}$ virus particles per dosage unit. However, alternative formulations are also deemed suitable for use herein, and all known routes and modes of administration are contemplated herein. Where the pharmaceutical composition includes the recombinant bacteria, it is preferred that the bacteria titer of the composition $10^2$-$10^3$, $10^3$-$10^4$, $10^4$-$10^5$ bacteria cells per dosage unit. Where the pharmaceutical composition includes the recombinant yeast, it is preferred that the bacteria titer of the composition $10^2$-$10^3$, $10^3$-$10^4$, $10^4$-$10^5$ yeast cells per dosage unit.

As used herein, the term "administering" a virus, bacterial or yeast formulation refers to both direct and indirect administration of the virus, bacterial or yeast formulation, wherein direct administration of the formulation is typically performed by a health care professional (e.g., physician, nurse, etc.), and wherein indirect administration includes a step of providing or making available the formulation to the health care professional for direct administration (e.g., via injection, infusion, oral delivery, topical delivery, etc.).

In some embodiments, the virus, bacterial or yeast formulation is administered via systemic injection including subcutaneous, subdermal injection, or intravenous injection. In other embodiments, where the systemic injection may not be efficient (e.g., for brain tumors, etc.), it is contemplated that the formulation is administered via intratumoral injection.

With respect to dose and schedule of the formulation administration, it is contemplated that the dose and/or schedule may vary depending on depending on the type of virus, bacteria or yeast, type and prognosis of disease (e.g., tumor type, size, location), health status of the patient (e.g., including age, gender, etc.). While it may vary, the dose and schedule may be selected and regulated so that the formulation does not provide any significant toxic effect to the host normal cells, yet sufficient to be elicit immune response. Thus, in a preferred embodiment, an optimal or desired condition of administering the formulation can be determined based on a predetermined threshold. For example, the predetermined threshold may be a predetermined local or systemic concentration of specific type of cytokine (e.g., IFN-γ, TNF-β, IL-2, IL-4, IL-10, etc.).

For example, where the pharmaceutical composition includes the recombinant virus, the contemplated dose of the oncolytic virus formulation is at least $10^6$ virus particles/day, or at least 108 virus particles/day, or at least $10^{10}$ virus particles/day, or at least $10^{11}$ virus particles/day. In some embodiments, a single dose of virus formulation can be administered at least once a day or twice a day (half dose per administration) for at least a day, at least 3 days, at least a week, at least 2 weeks, at least a month, or any other desired schedule. In other embodiments, the dose of the virus formulation can be gradually increased during the schedule, or gradually decreased during the schedule. In still other embodiments, several series of administration of virus formulation can be separated by an interval (e.g., one administration each for 3 consecutive days and one administration each for another 3 consecutive days with an interval of 7 days, etc.).

In some embodiments, the administration of the pharmaceutical formulation can be in two or more different stages: a priming administration and a boost administration. It is contemplated that the dose of the priming administration is higher than the following boost administrations (e.g., at least 20%, preferably at least 40%, more preferably at least 60%). Yet, it is also contemplated that the dose for priming administration is lower than the following boost administrations. Additionally, where there is a plurality of boost administration, each boost administration has different dose (e.g., increasing dose, decreasing dose, etc.).

With respect to contemplated cytotoxic cell components, it should be noted that the cell components are preferably NK cells (and all derivatives thereof), NKT cells, and/or cytotoxic T cells (e.g., CD8+ T cells, etc.). In some embodiments, the cytotoxic cell components may comprise NK, NKT, or cytotoxic T cells that are naive to the patient or allogeneic. For example, NK cells may also be obtained from the patient or produced from precursor cells of the patient, or obtained from a cell bank (preferably allotype matched). In further examples, the cell component may also be an activated T cell, which may be isolated from the patient (and optionally reactivated where anergic), or from a donor or cell culture. Where appropriate, such T cells may also be genetically modified to express a chimeric antigen receptor and/or CD16 to increase specificity of the cell to a tumor cell. In other embodiments, the cytotoxic cell components may comprise heterologous cells to the patients, preferably immortalized, genetically engineered cells. For example, especially contemplated NK cells include aNK cells (activated NK-92 derivative cells lacking multiple inhibitory receptors), haNK cells (NK-92 derivative cells with high affinity CD16 variant (e.g., V158 variant, etc.), and tank cells (NK-92 derivative cells with chimeric antigen receptor), which are known in the art (e.g., NantKwest, Inc., 9920 Jefferson Blvd.; Culver City, Calif. 90232). In addition, it is also preferred that the NK92 cell is further genetically modified to express and intracellularly retain IL-2 (e.g., in the endoplasmic reticulum) such that the cytotoxicity of NK cell remains active under hypoxic conditions (e.g., tumor microenvironment).

It should be particularly appreciated that where haNK cells are employed in contemplated methods, cytotoxic activity of the haNK cells in hypoxic environment is in large part maintained, which is especially advantageous in the typically hypoxic tumor microenvironment. Therefore, especially preferred methods include administration of haNK cells, with or without antibodies coupled to the haNK cells. Viewed from a different perspective, targeted cytolytic activity can be achieved in the tumor microenvironment, even where the milieu is hypoxic. Moreover, activity of haNK cell killing can be further increased or at least preserved by aldoxorubicin as is further discussed in more detail below.

Contemplated cytotoxic cells are typically administered to the patient in an amount of between $1-5 \times 10^9$ cells per transfusion, and where haNK cells are used, it should be appreciated that these cells may be 'loaded' with an antibody or a protein to so impart target specificity or elicit and/or facilitate immune response in the tumor. As will be readily appreciated, such 'loading' will be achieved by binding the antibody to the high-affinity variant of CD16 on the haNK cell. Alternatively or additionally, it should be noted that the antibodies may be administered separately from the cytotoxic cells, and all manners of administration are deemed suitable for use herein (e.g., intravenous injection).

Any suitable antibodies that can specifically target tumor cells are contemplated. Exemplary antibodies may include those specifically and/or selectively bind to a growth factor receptor (e.g., HER2, etc.), a blood vessel growth receptor (e.g., VEGFR-1, VEGFR-2, etc.), a tumor associated antigen, a tumor specific antigen, and a tumor- and patient-specific neoepitope. For example, contemplated haNK cells may be associated with cetuximab (binding to EGFR) or co-administered with cetuximab. In addition, the cytotoxic cells can be loaded with, or co-administered with a binding protein to an immune checkpoint inhibitor, which may include an antibody or an antagonist of CTLA-4, PD-1, TIM1 receptor, 2B4, or CD160.

In some embodiments, the antibodies and/or a protein antagonistic to the immune checkpoint inhibitor may be coupled to the cytotoxic immune cell via a linker, either cleavable or non-cleavable, and/or directly or indirectly. For example, a linker can be a short length peptide, which is between 3-30 amino acids, preferably between 5-20 amino acids, more preferably between 5-15 amino acids. Preferably, such short peptide linker has glycine-rich sequences (e.g., gly-gly-ser-gly-gly, etc.) to provide flexibility. In another example, a linker can be a cleavable linker that is preferentially cleaved in the tumor microenvironment and/or upon activation of immune system are contemplated. One preferred cleavable linker is cleavable in a mild acidic environment (e.g., at a pH between 3-6, at a pH between 4-6, at a pH between 4.5-5.5, etc.), yet stable in a neutral pH. For example, preferred acid-labile linkers include a thimaleamic acid linker and an acid-cleavable hydrazine linker (e.g., hydrazine linker, etc.). It is contemplated that antibodies or binding proteins/molecules coupled to the cytotoxic immune cell via an acid-labile linker can be released in the mildly acidic tumor microenvironment, such that the antibodies or binding proteins/molecules can selectively and specifically target tumor cells in the tumor microenvironment.

So contemplated linkers can be directly or indirectly coupled to the immune competent cell. With respect to the direct coupling of the linkers, the method of conjugating the linker to the cell may vary depending on the chemical structure and component of the linker, and any suitable methods for conjugation are contemplated. In some embodiments, the linker can be directly conjugated to a membrane protein of the immune competent cell, preferably without interfering the normal function of the cell. It is further preferred that the cell membrane protein to couple the linker has a relatively longer half-life span such that the coupled linker may not be endocytosed due to the recycling of the membrane protein. In such embodiments, the linker can be conjugated to the N-hydroxysuccinimidyl-PEG (PEG-NETS), by which the linker covalently bonds with all kinds of membrane proteins having amino groups on cell surfaces. Alternatively, the linker can be conjugated with PEG to form PEG-glycolipid or with poly(vinyl alcohol) carrying alkyl side chains (PVA-alkyl) such that the conjugated linker can anchor to the membrane lipid bilayer of the immune competent cell through hydrophobic interactions.

Moreover, it is contemplated that the methods and uses presented herein may be further augmented with one or more immune stimulatory and/or cytokines immune stimulatory superkines. Especially preferred cytokines include IL-2, IL-7, IL-15, IL-17, IL-21, IL-15, IPS1, and LMP1, and superagonist versions thereof. For example, where a superkine an IL-15 superagonist (IL-15N72D), and/or an IL-15 superagonist/IL-15RαSushi-Fc fusion complex (ALT803) are especially preferred.

Most preferably, contemplated compounds and compositions are administered using a temporal/spatial orchestration of a combination of immunotherapeutic products to modulate the tumor microenvironment, to activate the innate adaptive immune system, and to further induce immunogenic cell death (ICD), all of which may be (synergistically) enhanced by aldoxorubicin. In this context, it should be particularly recognized that aldoxorubicin is a maleimido-caproyl hydrazone prodrug form of doxorubicin, which comprises a reactive group that covalently binds to available thiol groups (e.g., C34 in albumin) and that has an acid labile hydrazine bond that, upon hydrolytic cleavage, released doxorubicin. Thus, upon exposure of aldoxorubicin to the hypoxic acidic tumor microenvironment, doxorubicin is preferentially released into the tumor microenvironment. Such preference is further enhanced by coupling of aldoxorubicin to albumin, which is recycled into the tumor microenvironment (typically via gp60 mediated transcytosis). It is known that in certain cancers, myeloid-derived suppressor cells (MDSCs) play vital roles in promoting tumor progression, chiefly because of their 'alternatively activated' (or M2) phenotype that orchestrates immunosuppression. Advantageously, doxorubicin counteracts M2 macrophages and MDSC.

To that end, and among other contemplated options, preferred treatment components may include (a) nanoparticle albumin bound (Nab) chemotherapy combinations to enter the tumor microenvironment (e.g., via transcytosis) to overcome the tumor suppressor environment, (b) antigen producing vaccine entities (e.g., recombinant adenovirus, bacteria, and/or yeast) that directly or indirectly deliver tumor associated antigens and/or patient- and tumor-specific neoantigens to immune competent cells to activate immature dendritic cells in a patient and tumor specific manner to induce and/or enhance an adaptive immune response, (c) natural killer cells, which may be endogenous (e.g., by stimulation with IL-15 or IL-15 superagonist) and/or exogenous (e.g., genetically modified NK cells such as aNK, haNK, taNK cells) to induce and/or enhance an innate immune response, and (d) endogenous activated memory T- and/or NK-cells to sustain long term remission, preferably activated via vaccine, cell therapy, and fusion proteins (e.g., genetically engineered fusion protein cytokine stimulators and/or checkpoint inhibitors).

Any suitable orders of administering immune therapeutic composition (vaccine component and a cytotoxic cell component) and a chemotherapeutic composition (aldoxorubicin) are contemplated. For example, both immune therapeutic composition and chemotherapeutic compositions can be administered to the patient concurrently or same day (e.g., within 1 hour, within 3 hours, within 6 hours, within 12 hours, within 24 hours, etc.) or different days (e.g., at least 1 day apart, at least 2 days apart, etc.). Most preferred schedules of administration of the compositions are provided in the example below.

are overexpressed or underexpressed in tumor tissues (e.g., HER2). Any suitable methods of obtaining genomics and/or transcriptomics profile of the patient's tumor are contemplated. Especially preferred methods include identifying and/or quantifying one or more cell free DNA and/or cell free RNA derived from the tumor-associated genes obtained from patient's bodily fluid (e.g., serum, whole blood, etc.) and determining their relationship with the molecular characteristic of the tumor and/or tumor prognosis.

EXAMPLES

Example I: Immunotherapy in Subjects with Advanced Chordoma

Therapeutic compositions and modalities used in Example I include various biological molecules and compositions as shown in Table 1 below.

TABLE 1

| | |
|---|---|
| ALT-803 | Recombinant human super agonist interleukin-15 (IL-15) complex, IL-15N72D:IL-15RαSu/IgG1 Fc complex (Altor Bioscience Corp., 2810 N Commerce Pkwy, Miramar, FL 33025) |
| ETBX-051 | Recombinant Adenovirus (Ad5 [E1-, E2b-]-Brachyury) that encodes Brachyury for expression of Brachyury in infected cells |
| ETBX-061 | Recombinant Adenovirus (Ad5 [E1-, E2b-]-MUC1) that encodes MUC1 for expression of MUC1 in infected cells |
| GI-6301 | Heat-killed *S. cerevisiae* yeast expressing the human Brachyury (hBrachyury) oncoprotein |
| NK-92[CD16.158V, ER IL-2] | NK92 derivative cells with high affinity CD16 variant and recombinant intracellular expression of IL-2 (high-affinity activated Natural Killer cells, [haNK ™], NantKwest, 9920 Jefferson Blvd. Culver City, CA 90232) |
| Aldoxorubicin | Doxorubicin derivative ((6-maleimidocaproyl) hydrazone of doxorubicin). |
| Bevacizumab | Avastin (VEGF antibody) |
| Cetuximab | ERBITUX ® injection, for IV infusion |
| Trabectedin | Yondelis ® for injection, for IV use |
| Avelumab | Bavencio (Fully human anti-PD-L1 IgG1 lambda monoclonal antibody) |
| Cyclophosphamide | 2-[bis(2-chloroethyl)amino]tetrahydro-2H-1,3,2-oxazaphosphorine 2-oxide monohydrate |
| Abraxane | Nab-paclitaxel (albumin bound paclitaxel) |
| Omega-3-acid ethyl esters | Lovaza (Omega-3-acid ethyl esters) |
| Radiation | Stereotactic Body Radiation Therapy (SBRT); 8 Gy maximum (exact dose to be determined by the radiation oncologist) |

The inventors generally contemplate that the treatments presented herein will be suitable for various cancers, including solid cancers and blood-borne cancers of mammals, and especially human. In addition, the inventors further contemplate that the treatments presented herein will be suitable for the patients whose tumor cells express a tumor-associated antigen, a tumor-specific antigen, and/or tumor- and patient-specific neoepitope that the vaccine component and/or cytotoxic cell components should target. Viewed from a different perspective, the inventors contemplate that a molecular profile of the patient's tumor cell can be determined prior and/or after the treatments to identify the most suitable vaccine component and/or cytotoxic cell components for treatment, to predict the likelihood of success of the treatment, and/or to determine the effectiveness of the treatment. Thus, the molecular profile may include a genomics profile of one or more tumor-associated genes, especially one or more mutations in such tumor-associated genes that are identified from the patient's tumor and/or known in the art (e.g., G12V, Q61R and/or Q61L mutations in RAS, etc.). Suitable molecular profiles may also include a transcriptomics profile of one or more tumor-associated genes that Treatment is administered in 2 phases, an induction and a maintenance phase, as described below. Subjects continue induction treatment for up to 1 year or until they experience progressive disease (PD) or unacceptable toxicity (not correctable with dose reduction). Those who have a complete response (CR) in the induction phase enter the maintenance phase of the study. Subjects may remain in the maintenance phase of the study for up to 1 year. Treatment continues in the maintenance phase until the subject experiences PD or unacceptable toxicity (not correctable with dose reduction). The maximum time on study treatment, including both the induction and maintenance phases, is 2 years.

Tumor biopsies and exploratory tumor molecular profiling can be conducted at screening, at the end of the initial induction phase (8 weeks after the start of treatment), and during potential prolonged induction and maintenance phases (depending on response). Separate blood tubes can be collected every 4 weeks in the induction phase and every 8 weeks in the maintenance phase during routine blood draws for exploratory immunology and ctDNA/ctRNA analyses. Tumors are assessed at screening, and tumor response are assessed every 8 weeks during the induction phase and every 12 weeks during the maintenance phase by computed tomography (CT), magnetic resonance imaging (MRI), or positron emission tomography (PET)-CT of target and non-target lesions in accordance with Response Evaluation Criteria in Solid Tumors (RECIST) Version 1.1 and immune-related response criteria (irRC).

Induction Phase:

The induction phase consists of repeated 2-week cycles for a maximum treatment period of 1 year. The treatment regimen includes ALT-803, avelumab, bevacizumab, cetuximab, cyclophosphamide, aldoxorubicin, ETBX-051, ETBX-061, GI-6301, haNK cells, nab-paclitaxel, omega-3-acid ethyl esters, trabectedin, and radiation therapy. Concurrent SBRT will be given during the first four 2-week cycles. Radiation is administered to no more than 5 feasible tumor sites using SBRT. The induction phase of study treatment is conducted in accordance with the following dosing regimen:

Daily: Omega-3-acid ethyl esters (by mouth [PO] twice a day [BID] [3×1 g capsules and 2×1 g capsules]).

Day 1, every 2 weeks: Bevacizumab (5 mg/kg IV).

Days 1-5 and 8-12, every 2 weeks: Cyclophosphamide (50 mg PO BID).

Day 1 and 8, every 2 weeks: Nab-paclitaxel (75 mg IV); Aldoxorubicin (25 mg/m² IV); Trabectedin (0.2 mg/m² IV).

Day 5, 19, 33 (every 2 weeks for 3 doses then every 8 weeks thereafter): ETBX-051 and ETBX-061 (5×10¹¹ virus particles [VP]/vaccine/dose subcutaneously [SC]); GI-6301 (40 yeast units [YU]/vaccine/dose SC), 2 hours after administration of ETBX-051/ETBX-061.

Day 8, every week: Cetuximab (250 mg IV).

Day 8, every 2 weeks: Avelumab (10 mg/kg IV over 1 hour).

Day 8, 22, 36, 50 (every 2 weeks for 4 doses): SBRT (not to exceed 8 Gy, exact dose to be determined by the radiation oncologist).

Day 9, every 2 weeks: ALT-803 (10 µg/kg SC 30 minutes prior to haNK infusion).

Day 9 and 11, every 2 weeks: haNK (2×10⁹ cells/dose IV).

Maintenance Phase:

The duration of the maintenance phase is up to 1 year following completion of the last treatment in the induction phase. The maintenance phase includes repeated 2-week cycles. The treatment regimen consists of ALT-803, avelumab, bevacizumab, cetuximab, cyclophosphamide, ETBX-051, ETBX-061, GI-6301, haNK cells, nab-paclitaxel, omega-3-acid ethyl esters, and trabectedin. The maintenance phase of study treatment will be conducted in accordance with the following dosing regimen:

Daily: Omega-3-acid ethyl esters (PO BID [3×1 g capsules and 2×1 g capsules]).

Day 1, every 2 weeks: Bevacizumab (5 mg/kg IV); Nab-paclitaxel (75 mg IV); Avelumab (10 mg/kg IV over 1 hour); Cetuximab (250 mg IV); Trabectedin (0.2 mg/m² IV).

Days 1-5 and 8-12, every 2 weeks: Cyclophosphamide (50 mg PO BID).

Day 2, every 2 weeks: ALT-803 (10 µg/kg SC) (30 minutes prior to haNK infusion); haNK (2×10⁹ cells/dose IV).

Day 5, every 8 weeks thereafter: ETBX-051 and ETBX-061, (5×10¹¹ VP/vaccine/dose SC); GI-6301 (40 YU/vaccine/dose SC), 2 hours after administration of ETBX-051.

Further methods, compositions, uses, and considerations suitable for use herein are described in our co-pending International patent application serial number PCT/US17/40297, filed 30 Jun. 2017.

Example II: NANT Squamous Cell Carcinoma (SCC) Vaccine

Molecularly informed integrated immunotherapy combining innate high-affinity natural killer (haNK) cell therapy with adenoviral and yeast-based vaccines to induce T-cell responses in subjects with SCC who have progressed on or after platinum-based chemotherapy and anti-programmed cell death protein 1 (PD-1)/programmed death-ligand 1 (PD-L1) therapy.

Therapeutic compositions and modalities used in Example II include various biological molecules and compositions as shown in Table 2 below.

TABLE 2

| | |
|---|---|
| ALT-803 | Recombinant human super agonist interleukin-15 (IL-15) complex, IL-15N72D:IL-15RαSu/IgG1 Fc complex (Altor Bioscience Corp., 2810 N Commerce Pkwy, Miramar, FL 33025) |
| ETBX-011 | Recombinant Adenovirus (Ad5 [E1-, E2b-]- carcinoembryonic antigen [CEA]) that encodes Brachyury for expression of CEA in infected cells |
| ETBX-021 | Recombinant Adenovirus (Ad5 [E1-, E2b-]- human epidermal growth factor receptor 2 [HER2]) that encodes Brachyury for expression of HER2 in infected cells |
| ETBX-051 | Recombinant Adenovirus (Ad5 [E1-, E2b-]-Brachyury) that encodes Brachyury for expression of Brachyury in infected cells |
| ETBX-061 | Recombinant Adenovirus (Ad5 [E1-, E2b-]-MUC1) that encodes MUC1 for expression of MUC1 in infected cells |
| GI-4000 | Heat-killed *S. cerevisiae* yeast expressing the human Ras |
| GI-6207 | Heat-killed *S. cerevisiae* yeast expressing the human CEA |
| GI-6301 | Heat-killed *S. cerevisiae* yeast expressing the human Brachyury (hBrachyury) oncoprotein |
| NK-92[CD16.158V, ER IL-2] | NK92 derivative cells with high affinity CD16 variant and recombinant intracellular expression of IL-2 (high-affinity activated Natural Killer cells, [haNK ™], NantKwest, 9920 Jefferson Blvd. Culver City, CA 90232) |
| Aldoxorubicin | Doxorubicin derivative ((6-maleimidocaproyl) hydrazone of doxorubicin). |
| Bevacizumab | Avastin (VEGF antibody) |
| Capecitabine | Xeloda ® tablets, for oral use |
| Cetuximab | ERBITUX ® injection, for IV infusion |
| Cisplatin | CISplatin injection |
| Trabectedin | Yondelis ® for injection, for IV use |

TABLE 2-continued

| | |
|---|---|
| Avelumab | Bavencio (Fully human anti-PD-L1 IgG1 lambda monoclonal antibody) |
| Necitumumab | Portrazza ® injection |
| 5-Fluorouracil | 5-FU; Fluorouracil Injection, for IV use only |
| Leucovorin | LEUCOVORIN Calcium for Injection, for IV or intramuscular [IM] use |
| Nab-paclitaxel | ABRAXANE ® for Injectable Suspension [paclitaxel protein-bound particles for injectable suspension] [albumin-bound] |
| Radiation | Stereotactic Body Radiation Therapy (SBRT); 8 Gy maximum (exact dose to be determined by the radiation oncologist) |

The treatments in this example are provided to the patients who had previously treated with, and whose tumors have progressed on or after, platinum-based chemotherapy and anti-PD-1/PD-L1 therapy. Treatment in this example is administered in 2 phases, an induction and a maintenance phase, as described below. Subjects continue induction treatment for up to 1 year. Those who have a complete response (CR) in the induction phase enter the maintenance phase of the study. Subjects who experience ongoing stable disease (SD) or an ongoing partial response (PR) at 1 year may enter the maintenance phase. Subjects may remain in the maintenance phase of the study for up to 1 year. Treatment continues in the maintenance phase until the subject experiences PD or unacceptable toxicity (not corrected with dose reduction), withdraws consent, or if it is no longer in the subject's best interest to continue treatment. The time on study treatment, including both the induction and maintenance phases, is up to 2 years.

Exploratory tumor molecular profiling is conducted on samples collected prior to treatment on this study, 8 weeks after the start of treatment, and during potential prolonged induction and maintenance phases (depending on response). Separate blood tubes are collected every 6 weeks in the induction phase and every 8 weeks in the maintenance phase during routine blood draws for exploratory immunology and ctDNA/ctRNA analyses.

Tumors are assessed at screening, and tumor response are assessed every 8 weeks during the induction phase, and every 12 weeks during the maintenance phase by computed tomography (CT), magnetic resonance imaging (MM), or positron emission tomography-computed tomography (PET-CT) of target and non-target lesions in accordance with Response Evaluation Criteria in Solid Tumors (RECIST).

Prospective tumor molecular profiling is conducted to inform HER2 expression and RAS mutational status and will be used to determine whether ETBX-021 and GI-4000 will be administered. ETBX-021 and GI-4000 administration can be initiated as soon as results from tumor molecular profiling are available. All subjects receive all other agents regardless of their tumor molecular profile. Prospective tumor molecular profiling can be also performed on FFPE tumor tissue and whole blood (subject-matched normal comparator against the tumor tissue) collected prior to treatment on this study). Subjects receive ETBX-021 if their tumor overexpresses HER2 (≥750 attomole/µg of tumor tissue, as determined by quantitative proteomics with mass spectrometry). Subjects receive GI-4000 if their tumor is positive for specific RAS mutations, as determined by whole genome sequencing.

The treatment regimen in this example is in 2 phases: an induction phase and a maintenance phase. The purpose of the induction phase is to stimulate immune responses against tumor cells and mitigate immunosuppression in the tumor microenvironment. The purpose of the maintenance phase is to sustain ongoing immune system activity against tumor cells, creating durable treatment responses.

Induction Phase:

Treatment in the induction phase consist of repeated 3-week cycles for a maximum treatment period of 1 year, shown in the treatment regimen as follows:

Day 1, every 3 weeks: Bevacizumab (5 mg/kg IV), Leucovorin (20 mg/m$^2$ IV bolus), Nab-paclitaxel (125 mg IV), Cisplatin (40 mg/m$^2$ IV over 1 hour).

Days 1-5, every 3 weeks: 5-FU (1,500 mg/m$^2$ continuous IV infusion over 85-96 hours), Cyclophosphamide (25 mg by mouth [PO] twice a day [BID])

Day 5 (±1 day), every 3 weeks for 3 cycles then every 9 weeks thereafter: ETBX-011, ETBX-021, ETBX-051, and ETBX-061 (1×10$^{11}$ virus particles [VP]/vaccine/dose subcutaneously [SC]).

It should be appreciated that prospective tumor molecular profiling can determine whether ETBX-021 will be administered, as described above.

Day 8: Aldoxorubicin HCl (80 mg/m$^2$ IV over 30 minutes), Cisplatin (20 mg/m$^2$ IV over 1 hour), SBRT (not to exceed 8 Gy, exact dose to be determined by the radiation oncologist; for the first 2 cycles only), and Cetuximab (250 mg/m$^2$ IV) or necitumumab (400 mg IV). It is noted that Cetuximab will be administered to subjects with head and neck squamous cell carcinoma (HNSCC), while necitumumab will be administered to subjects with squamous non-small cell lung cancer (NSCLC).

Days 8-12, every 3 weeks: Cyclophosphamide (25 mg PO daily [QD]).

Day 9, every 3 weeks: Avelumab (10 mg/kg IV over 1 hour), ALT-803 (10 µg/kg SC at least 30 minutes prior to haNK infusion), haNK (2×10$^9$ cells/dose IV).

Day 11, every 3 weeks: haNK (2×10$^9$ cells/dose IV).

Day 11, every 3 weeks for 3 cycles and every 9 weeks thereafter: GI-4000, GI-6207, GI-6301, (40 yeast units [YU]/vaccine/dose SC). Prospective tumor molecular profiling will determine whether GI-4000 will be administered, as described above.

Day 15, every 3 weeks: SBRT (not to exceed 8 Gy, exact dose to be determined by the radiation oncologist; for the first 2 cycles only).

Day 16, every 3 weeks: ALT-803 (10 µg/kg SC at least 30 minutes prior to haNK infusion), haNK (2×10$^9$ cells/dose IV), Cetuximab (250 mg/m$^2$ IV) or necitumumab (400 mg IV).

Day 18, every 3 weeks: haNK (2×10$^9$ cells/dose IV).

Maintenance Phase:

The duration of the maintenance phase will be up to 1 year following completion of the last treatment in the induction phase. The maintenance phase will consist of repeated 2-week cycles, shown in the treatment regimen as follows:

Day 1, every 2 weeks: Aldoxorubicin HCl (60 mg/m$^2$ IV over 30 minutes), Bevacizumab (5 mg/kg IV), Nab-paclitaxel (100 mg IV).

Days 1-5, every 2 weeks: Capecitabine (650 mg/m² PO BID).

Days 1-5 and 8-12, every 2 weeks: Cyclophosphamide (25 mg PO BID).

Day 2, every 2 weeks: Avelumab (10 mg/kg IV over 1 hour), Cetuximab (250 mg/m² IV) or necitumumab (400 mg IV), ALT-803 (10 µg/kg SC) (at least 30 minutes prior to haNK infusion), haNK (2×10⁹ cells/dose IV). Cetuximab will be administered to subjects with HNSCC, while necitumumab will be administered to subjects with squamous NSCLC.

Day 5 (±1 day), every 8 weeks thereafter: ETBX-011, ETBX-021, ETBX-051, ETBX-061 (1×10¹¹ VP/vaccine/dose SC), GI-4000, GI-6207, GI-6301 (40 YU/vaccine/dose SC), 2 hours after administration of Ad-5 based vaccines.

The inventors contemplate, without wishing to be bound by any specific theory, that above treatment regimen that combines low-dose, metronomic chemotherapy (LMDC), bevacizumab, cetuximab or necitumumab, cancer vaccines, low-dose radiation therapy, an IL-15 superagonist, NK cell therapy, and a checkpoint inhibitor, can maximize immunogenic cell death (ICD) and augment and maintain the innate and adaptive immune responses against cancer cells. Specifically, the inventors contemplate that such treatment regime can interrupt the escape phase of immunoediting by 1) mitigating immunosuppression in the tumor microenvironment, 2) inducing and coordinating ICD signals, 3) conditioning dendritic and T cells, 4) enhancing innate immune response, and 5) maintaining immune responses.

More specifically, the inventors contemplate that immunosuppression in the tumor microenvironment can be mitigated as low-dose radiation therapy can reduce the density of Tregs, MDSCs, and M2 macrophages contributing to immunosuppression in the tumor microenvironment. Bevacizumab is also attributed to cause morphological changes in the tumor microenvironment to promote lymphocyte trafficking. ICD signals can be induced and coordinated as LDMC and low-dose radiation therapy can increase the antigenicity of tumor cells. In addition, Bevacizumab alters the TME, which allows for more efficient antigen-specific T-cell responses and makes tumor cells more susceptible to ICD. Further, Cetuximab, necitumumab, and avelumab will be used to enhance ADCC and cytotoxic T-cell activity.

The inventors further contemplate that dendritic cells and T cells can be conditioned by cancer vaccines and an IL-15 superagonist that enhance tumor-specific cytotoxic T-cell responses. In addition, innate immune responses can be enhanced by NK cell therapy that can augment the innate immune system, and by an IL-15 superagonist that can enhance the activity of endogenous and introduced NK cells. Hypofractionated-dose radiation therapy can upregulate tumor cell NK ligands to enhance tumor cytotoxicity of NK cells. Finally, the immune response can be maintained by a checkpoint inhibitor that can promote long-term anticancer immune responses. Thus, by combining agents that simultaneously target distinct but complementary mechanisms that enable tumor growth, the treatment regimen aims to maximize anticancer activity and prolong the duration of response to treatment.

The inventors discovered that such combinatorial treatment and the treatment regimen using a vaccine component, a cytotoxic cell component, and/or aldoxorubicin, is effective in treating a tumor in some patients diagnosed with metastasized cancer. In one example, a 35-year-old male patient diagnosed with pancreatic cancer with metastasis to liver and lung, and previously failed with standard chemotherapy, was treated with a combinatorial treatment of NANT cancer vaccine and cytotoxic immune cell (initially with aNK and evolved to cryopreserved haNKs) for 13 cycles. Levels of carbohydrate antigen (CA19-9) in the patient's blood were determined before and throughout the treatment. As shown in FIG. 1, the CA19-9 levels were significantly decreased from about 750 to about 220 during about 320 days of treatment. The patient also gained weight of 10 lbs and stayed in a pain-free condition. In addition, the size of the tumor was reduced during the 6.5 months since the initiation of the treatment. No dose-limiting toxicity (DLT) could be observed during the treatment.

Figure 2:
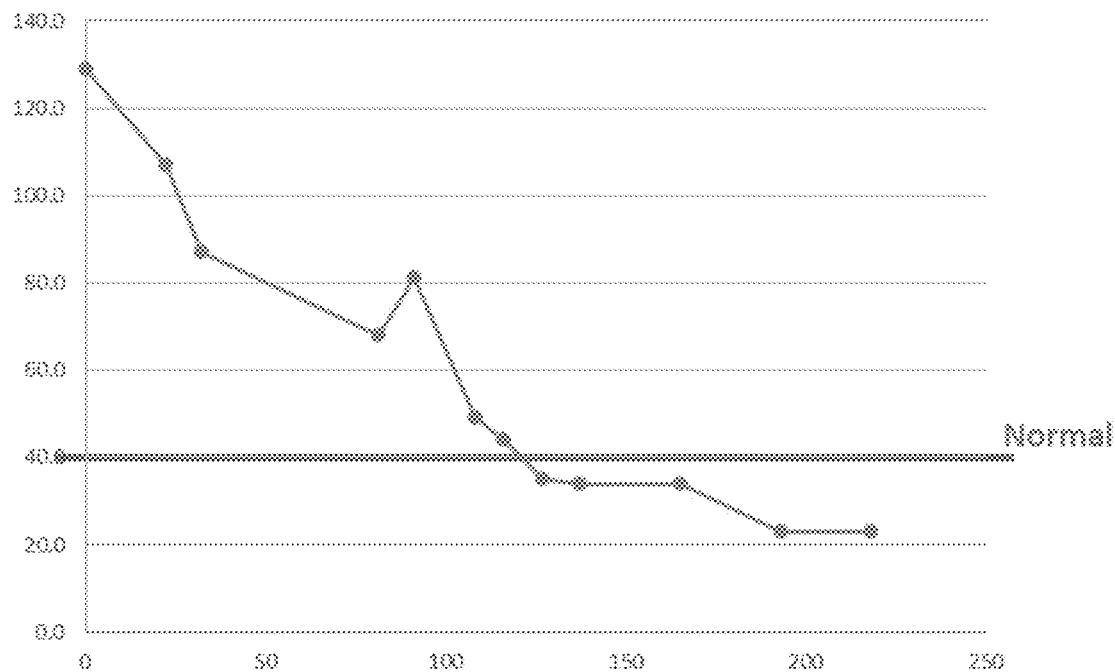
FIG. 2 shows a graph of normalized carbohydrate antigen (CA) 19-9 (CA19-9) level in patient's blood after cancer vaccine and cytotoxic cell treatment to patient #2 diagnosed with metastatic pancreatic cancer. The x-axis represents days (time) and y-axis represents quantity.

In another example, a 50-year-old female patient diagnosed with pancreatic cancer and previously failed with standard chemotherapy, was treated with a combinatorial treatment of NANT pancreatic cancer vaccine and cytotoxic immune cell (initially with aNK and evolved to cryopreserved haNKs) for 12 cycles. Levels of carbohydrate antigen (CA19-9) in the patient's blood were determined before and throughout the treatment. As shown in FIG. 2, the CA19-9 levels were significantly decreased from about 1300 to about 220 (from 129 to 34 in standardized value, more than 50%) during about 220 days of treatment. The patient also gained weight of 12 lbs and stayed in a pain-free condition. No dose-limiting toxicity (DLT) could be observed during the treatment.

Figure 3:
FIG. 3 shows a graph of carcinoembryonic antigen (CEA) level in patient's blood after cancer vaccine and cytotoxic cell treatment to patient #3 diagnosed with metastatic pancreatic cancer. The x-axis represents days (time) and y-axis represents quantity.

In still another example, a 63-year-old male patient diagnosed with pancreatic cancer with metastasis to liver, and previously failed with standard chemotherapy, was treated with a combinatorial treatment of NANT pancreatic cancer vaccine (e.g., see clinical trial identifier NCT03136406) and cytotoxic immune cell (initially with aNK and evolved to cryopreserved haNKs) for 8 cycles. Levels of CEA in the patient's blood were determined before and throughout the treatment. As shown in FIG. 3, the CEA levels were significantly decreased from about 450 to about 200 (from 45 to 20 in standardized value, more than 50%) during about 260 days of treatment. The patient stayed in a pain-free condition. No dose-limiting toxicity (DLT) could be observed during the treatment.

Figure 4:
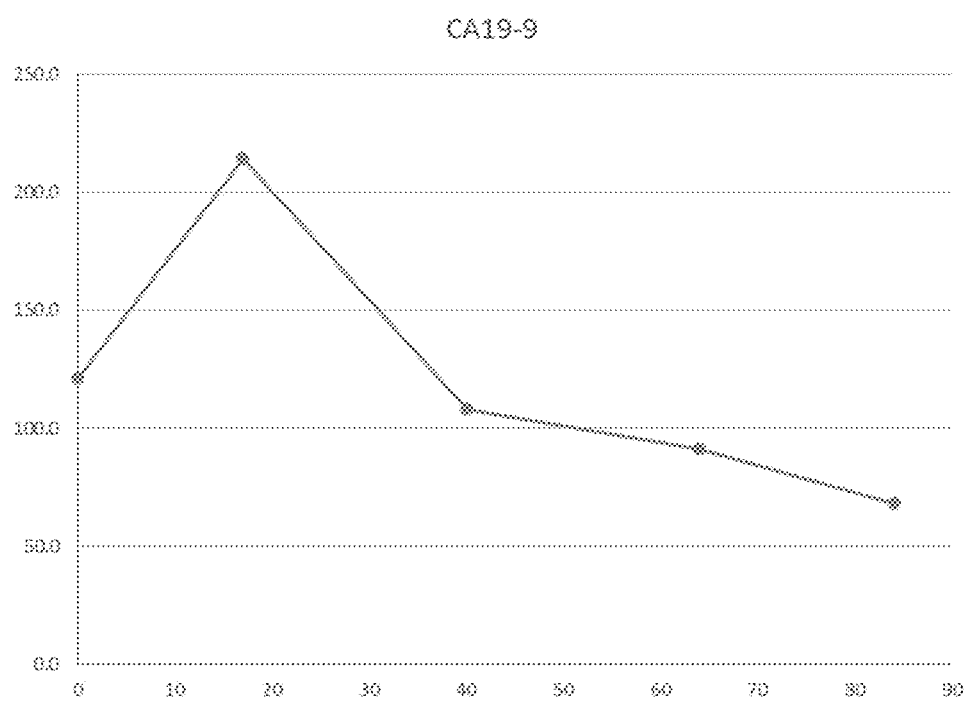
FIG. 4 shows a graph of normalized carbohydrate antigen (CA) 19-9 (CA19-9) level in patient's blood after cancer vaccine and cytotoxic cell treatment to patient #4 diagnosed with metastatic pancreatic cancer. The x-axis represents days (time) and y-axis represents quantity.

In still another example, a 66-year-old female patient diagnosed with pancreatic cancer with metastasis to liver and lung, and previously failed with standard care chemotherapy, was treated with a combinatorial treatment of NANT pancreatic cancer vaccine and cytotoxic immune cell (cryopreserved haNKs) for 4 cycles. Levels of carbohydrate antigen (CA19-9) in the patient's blood were determined before and throughout the treatment. As shown in FIG. 4, the CA19-9 levels were significantly decreased from about 1100 to about 650 (during about 85 days of treatment. No dose-limiting toxicity (DLT) could be observed during the treatment. The patient also showed 23% decrease of the tumor size per RECIST in 8 weeks of treatment.

Figure 5:
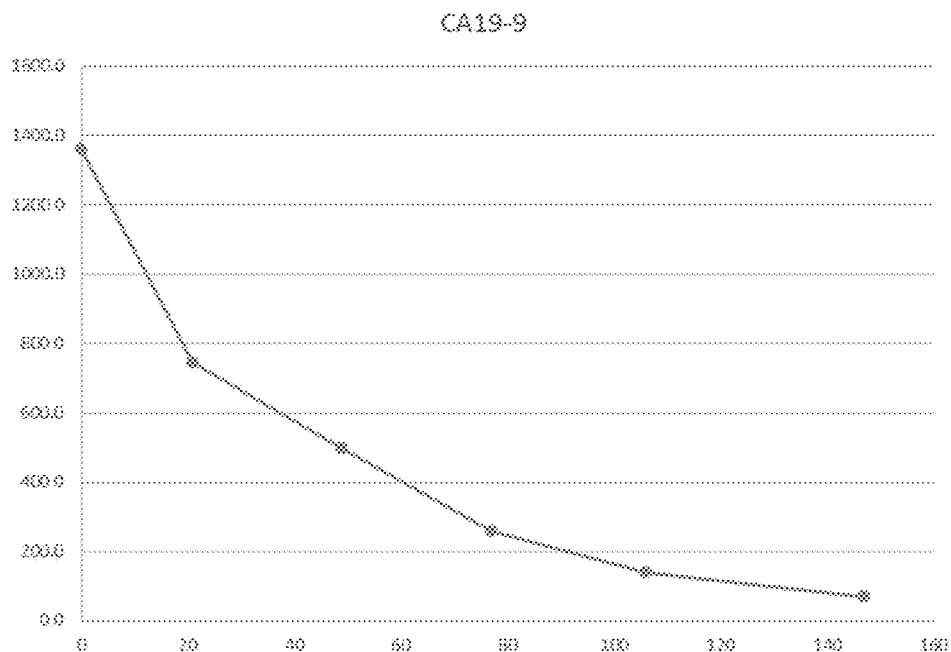
FIG. 5 shows a graph of normalized carbohydrate antigen (CA) 19-9 (CA19-9) level in patient's blood after cancer vaccine and cytotoxic cell treatment to patient #5 diagnosed with metastatic pancreatic cancer. The x-axis represents days (time) and y-axis represents quantity.

In still another example, a 40-year-old male patient diagnosed with pancreatic cancer with metastasis to liver and peritoneum, and previously failed with standard care chemotherapy, was treated with a combinatorial treatment of FOLFIRINOX (5-FU, leucovorin, irinotecan, and oxaliplatin) for 17 cycles and NANT pancreatic cancer vaccine and cytotoxic immune cell (cryopreserved haNKs) for 1 cycle. Levels of carbohydrate antigen (CA19-9) in the patient's blood were determined before and throughout the treatment. As shown in FIG. 5, the CA19-9 levels were significantly decreased from about 1400 to about 100 (during about 150 days of treatment. No dose-limiting toxicity (DLT) could be observed during the treatment.

Figure 6:
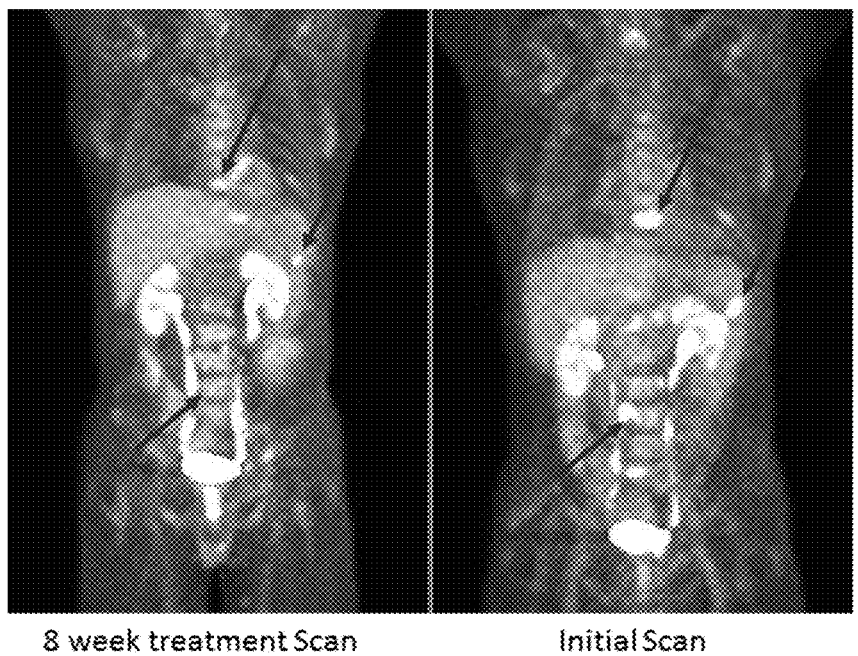
FIG. 6 shows PET scan photographs of patient #6 before and after cancer vaccine and cytotoxic cell treatment.
Figure 7:
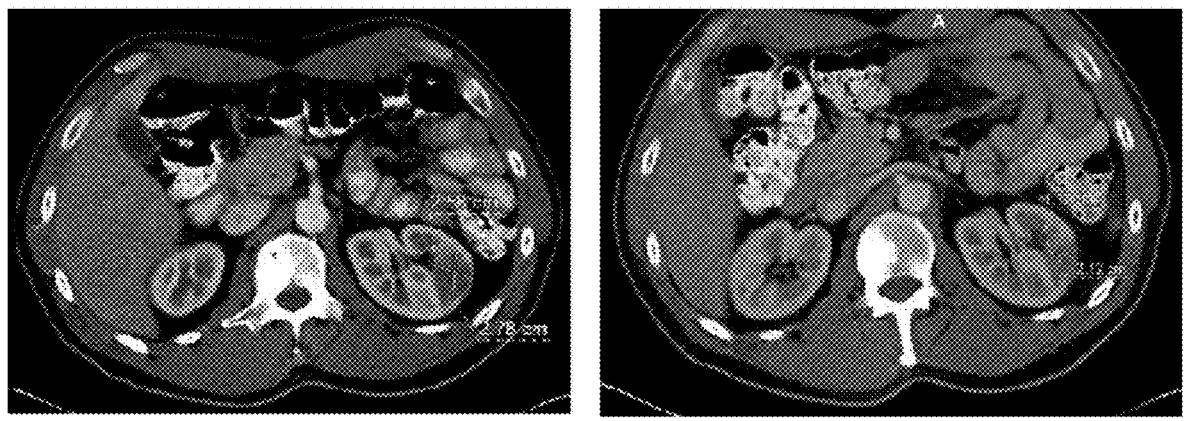
FIG. 7 shows transverse PET scan photographs of patient #6 before and after cancer vaccine and cytotoxic cell treatment.

In still another example, a 56-year-old male patient diagnosed with HNSCC (with a history of HPV). The patient was initially treated with cisplatin and radiation and later with Pembrolizumab and Nivolumab. The patient was treated with a treatment regimen as shown in Example II for 6 cycles. As shown in FIG. 6 (left is after treatment) and FIG. 7 (right is after treatment), the size of the non-irradiated renal target lesion was reduced by 46% in 8 weeks of treatment (as shown in arrows in FIG. 6, and shown in dotted area in FIG. 7).

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used herein, the phrase "at least one of A and B" is intended to refer to 'A' and/or 'B', regardless of the nature of 'A' and 'B'. For example, in some embodiments, 'A' may be single distinct species, while in other embodiments 'A' may represent a single species within a genus that is denoted 'A'. Likewise, in some embodiments, 'B' may be single distinct species, while in other embodiments 'B' may represent a single species within a genus that is denoted 'B'.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. The recitation of ranges of values herein is merely intended to serve as a shorthand method of referring individually to each separate value falling within the range. Unless otherwise indicated herein, each individual value with a range is incorporated into the specification as if it were individually recited herein.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a patient having a tumor, comprising:
    providing an immune therapeutic composition comprising
        (a) a vaccine component comprising adenoviral vectors encoding brachyury, MUC1, and CEA, (b) cetuximab, (c) a cytotoxic cell component comprising NK92 cells genetically modified to express a high affinity CD16 variant, and (d) ALT803, and further providing a chemotherapeutic composition comprising aldoxorubicin; and
    administering the immune therapeutic composition and the chemotherapeutic composition in a dose and schedule sufficient to treat the tumor.

2. The method of claim 1, further comprising administering an antibody to the patient or a protein that interferes with or down-regulates checkpoint inhibition.

3. The method of claim 2, wherein the antibody is coupled to the cytotoxic cell component.

4. The method of claim 2, wherein the antibody specifically binds to at least one of a growth factor receptor, a blood vessel growth receptor, an immune checkpoint inhibitor, a tumor associated antigen, a tumor specific antigen, or a tumor- and patient-specific neoepitope.

5. The method of claim 2, wherein the protein that interferes with or down-regulates checkpoint inhibition is an antibody or an antagonist of CTLA-4, PD-1, TIM1 receptor, 2B4, or CD160.

6. The method of claim 1, wherein the tumor is a solid tumor.

7. The method of claim 1, wherein the vaccine component and the cytotoxic cell component are separately administered by at least one day.

8. The method of claim 1, wherein the patient has a medical history of at least one of previous platinum-based chemotherapy and anti-PD-1/PD-L1 therapy.

9. The method of claim 1, further comprising determining a molecular profile of the patient, wherein the molecular profile comprises an HER2 expression level or a RAS mutation status.

10. The method of claim 1, wherein the tumor is metastatic Squamous Cell Carcinoma (SCC).

11. The method of claim 1, wherein the NK92 cells are high affinity NK (haNK) cells.

12. The method of claim 1, further comprising a vaccine component comprising yeast vectors expressing brachyury, Ras, and CEA.

* * * * *